United States Patent [19]  
Iwata et al.

[11] Patent Number: 4,944,746  
[45] Date of Patent: Jul. 31, 1990

[54] METHOD OF AND APPARATUS FOR SEPARATING A BALLOON IN A BALLOON CATHETER

[75] Inventors: Hiroo Iwata, Suita; Sen Yamagata, Kyoto; Waro Taki, Osaka; Takehisa Matsuda, Minoo; Haruhiko Kikuchi, Suita; Yasuhiro Yonekawa, Kyoto; Yasuhiro Goto, Aichi, all of Japan

[73] Assignee: Kabushiki-Kaisha Tokai-Rika-Denki-Seisakusho, Aichi, Japan

[21] Appl. No.: 322,923

[22] Filed: Mar. 14, 1989

[30] Foreign Application Priority Data

Mar. 18, 1988 [JP] Japan .................................. 63-65084

[51] Int. Cl.$^5$ ............................................ A61M 29/02
[52] U.S. Cl. .................................... 606/195; 606/194
[58] Field of Search ................... 128/325, 344; 604/96, 604/99, 100, 103, 97; 606/89, 144, 195, 194, 192

[56] References Cited

U.S. PATENT DOCUMENTS

Re. 32,348  2/1987  Pevsner ................................ 604/99
4,341,218  7/1982  Ü ........................................ 604/97
4,346,712  8/1982  Handa et al. ......................... 604/99

FOREIGN PATENT DOCUMENTS 3014236  7/1982  Fed. Rep. of Germany ...... 128/325

Primary Examiner—Lee S. Cohen  
Assistant Examiner—Kennedy J. Schaetzle  
Attorney, Agent, or Firm—Venable, Baetjer and Howard

[57] ABSTRACT

An apparatus for separating a balloon from a catheter member of a balloon is capable of melting and breaking a heat-meltable connecting member through which the balloon is connected to the catheter body by causing an electric current to flow between at least a pair of electrodes arranged on or in the vicinity of the connecting member. The apparatus has impedance measuring means for measuring the impedance of an electrode circuit including a pair of electrodes and lead lines connected to the electrodes, and judging means for comparing the measured value of the impedance with a predetermined reference range and capable of producing an abnormal signal when the measured value of the impedance does not fall within the predetermined reference range. The apparatus enables the operator to judge whether the electrode circuit is in safe condition, before changing the balloon with a settable liquid and to charge a settable liquid into the balloon only when the safe condition of the electrode circuit is confirmed, so that the balloon after the setting of the liquid can be separated from the catheter body without fail, thus eliminating any risk for the catheter body to dangerously remain in the living body.

13 Claims, 6 Drawing Sheets

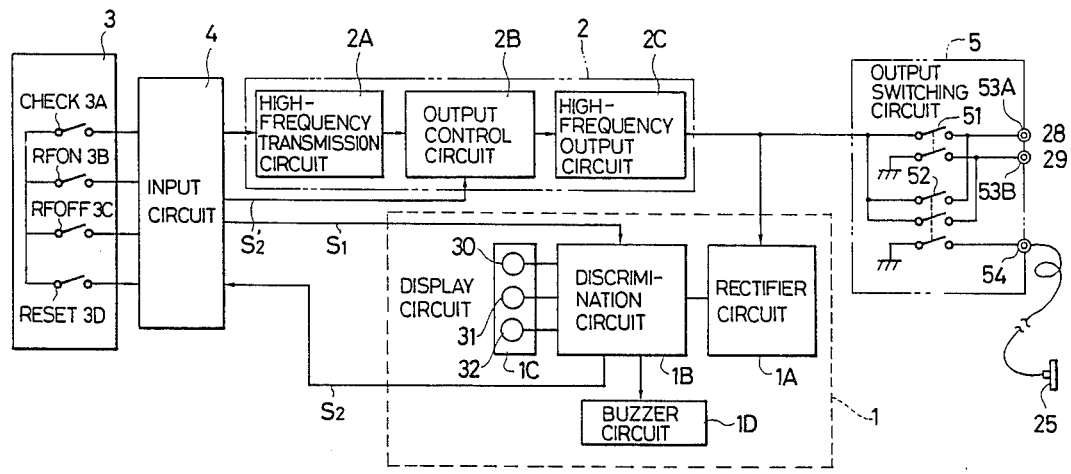

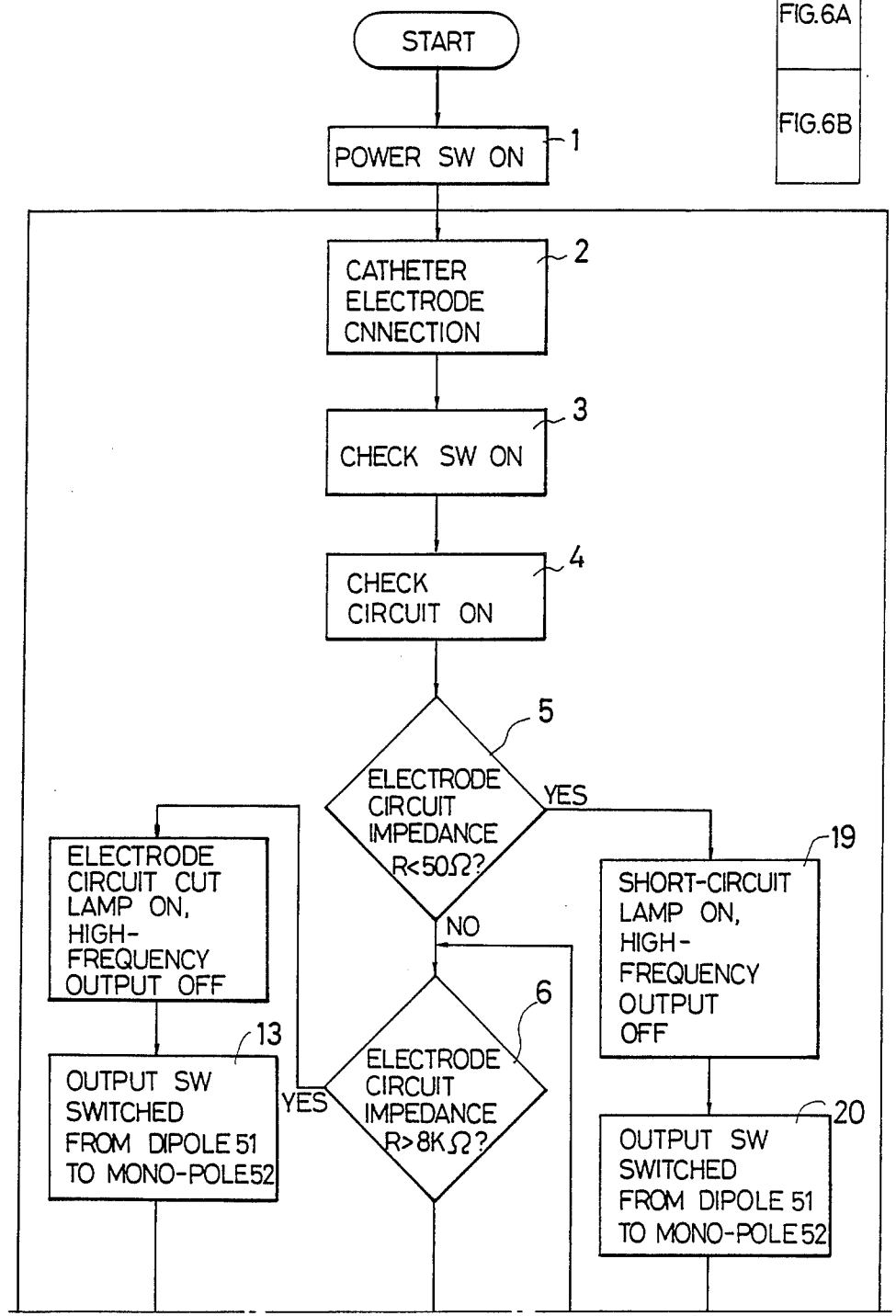

METHOD OF AND APPARATUS FOR SEPARATING A BALLOON IN A BALLOON CATHETER

BACKGROUND OF THE INVENTION

1. Field of the Invention

The present invention relates to a balloon catheter in which a balloon can indwell a blood vessel after being separated from a catheter body in response to a high-frequency electrical power. More particularly, the present invention is concerned with a method of and an apparatus for separating a balloon of a balloon catheter from the catheter body.

2. Description of the Related Art

A typical known balloon catheter has, as disclosed in Japanese Pat. Examined Publication No. 60-30225, a catheter body which is provided at its one end with a needle or connector, and a balloon which is connected to the catheter body through a connecting member. The connecting member through which the catheter body and the balloon are connected to each other is provided with a dipole electrode composed of a pair of electrode members. These electrode members are respectively connected through lead lines to lead terminals which are provided on the end of the catheter body adjacent to the needle.

The balloon on the end of the balloon catheter is made from a rubbery material and is adapted to be charged with a curable or settable liquid.

In use, the balloon catheter is guided through a blood vessel to reach an affected portion of the blood vessel and then the settable liquid is supplied into the balloon, whereby a treatment called embolization is conducted. This treatment is used in, for example, remedy of various cerebrovascular diseases such as cerebral aneurysm, intracanial srteriovenous malformation, carotid cavernous angioma and so forth. In general, sideration ages of these diseases are comparatively young. These diseases are generally completely curable when a suitable treatment is taken. In addition, in case of such diseases, the affected part can hardly be accessed by surgical means. These are the reasons why embolization by means of a balloon catheter is widely used in the remedy of these diseases. Usually, the balloon catheter is guided from a femoral artery and to the affected part through an observation of an X-ray image. Then, a settable liquid mainly composed of fibronogen is injected into the balloon and allows the liquid to set thereby embolizing the affected part. After the setting of the settable liquid, a high-frequency electrical power is supplied to the dipole electrode so as to melt and cut the connecting member. Thus, the connecting member is made of a meltable material and the balloon after the separation indwells the blood vessel.

This known balloon catheter requires a complicated catheter operation in order to guide the catheter to the affected part of the blood vessel which requires remedy. If any short-circuiting is taking place between the lead lines, the separation between the catheter body and the balloon after the setting of the settable liquid cannot be effected even by the supply of the electrical power to the electrode members on the catheter, with the result that the catheter body itself is dangerously left in the blood vessel together with the balloon.

SUMMARY OF THE INVENTION

Accordingly, an object of the present invention is to provide a high-frequency electrical power supply device capable of detecting any trouble in the electric system in a balloon catheter such as short-circuiting between the electrodes, cutting or short-circuiting of lead lines, and so forth, thereby overcoming the above-described problems of the prior art.

To this end, according to one aspect of the present invention, there is provided a method for separating a balloon from a catheter body of a balloon catheter of the type which has the catheter body and the balloon connected to the catheter body through a connecting member made of a heat-meltable material, the balloon being adapted to be charged with a settable liquid and then be separated from the catheter body as a result of melting of the connecting member by an electric current supplied between at least a pair of electrodes arranged on or in the vicinity of the connecting member, the method comprises the steps of: measuring the impedance of an electrode circuit which includes the electrodes and lead lines connected to the electrodes; comparing the measured value of the impedance with a predetermined reference range and judging that, when the measured value does not fall within the reference range, an abnormal condition exists in the electrode; and prohibiting the charging of the settable liquid into the balloon when existence of the abnormal condition is detected as a result of the judgment.

According to another aspect of the present invention, there is provided an apparatus for separating a balloon from a catheter body of a balloon catheter of the type which has the catheter body, the balloon and a heat-meltable connecting member through which the balloon is connected to the catheter body, the apparatus comprising: at least a pair of electrodes provided on or in the vicinity of the connecting member; a melting electric power circuit for supplying a melting electric current to the electrodes so as to heat-melt the connecting member; impedance measuring circuit for measuring the impedance of an electrode circuit including the electrodes and lead lines connected to the electrodes; and judging means for comparing the measured value of the impedance with a predetermined reference range and producing an abnormal signal indicative of occurrence of an abnormal state when the measured value of the impedance does not fall within the reference range.

The invention also provides an apparatus for separating a balloon from a catheter body of a balloon catheter, comprising: a switch circuit including first switch means for inputting a check instruction, and second switch means for inputting a balloon separation instruction; a high-frequency voltage generating circuit adapted to be started in response to the check instruction or the balloon separation instruction from the first switch means or the second switch means; an output control circuit for controlling the output of the high-frequency voltage generating circuit to a predetermined low level; at least a pair of electrodes disposed on or in the vicinity of a heat-meltable connecting member through which the balloon is connected to the catheter body, and lead lines connected to the electrodes; an output circuit connected to the electrodes through the lead lines and capable of delivering the high-frequency voltage output from the output control circuit to the electrodes; a rectifier circuit for rectifying the output voltage from the output circuit; judging means operative in response to the check instruction from the first switch mean and capable of comparing the output voltage from the rectifier circuit with a predetermined reference voltage range and producing an abnormal signal when the output voltage from the rectifier circuit does not fall within the predetermined reference range; and alarming means for generating an alarm in response to the abnormal signal.

The above and other objects, features and advantages of the present invention will become clear from the following description of the preferred embodiments when the same is read in conjunction with the accompanying drawings.

DESCRIPTION OF THE PREFERRED EMBODIMENTS

Figure 2:
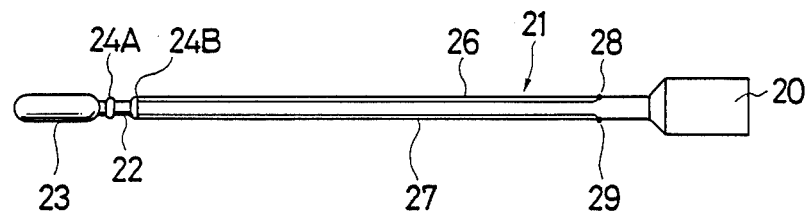
FIG. 2 is a plan view of a balloon catheter.

FIG. 2 is a plan view of a balloon catheter to which the present invention is applied. The balloon catheter has a catheter body 21 which is provided at its one end with a needle or connector 20, and a balloon 23 which is connected to the catheter body 21 through a connecting member 22. A dipole electrode composed of a pair of electrode members 24A and 24B is provided on the connecting member 22 through which the balloon 23 and the catheter body 21 are connected to each other. The electrode members 24A and 24B are respectively connected through lead lines 26, 27 to lead terminals 28 and 29 which are provided on the end of the catheter body 21 adjacent to the needle 20.

The balloon 23 on the end of the balloon catheter is made of a rubbery material and is adapted to be charged with a settable liquid. In use, the balloon catheter is introduced into and guided through a blood vessel to reach an affected part and then the settable liquid is charged to effect embolization. Usually, the balloon catheter is guided from a femoral artery and to the affected part through an observation of an X-ray image. After the supply and setting of the liquid in the catheter, high-frequency electrical power is supplied to the dipole electrode 24A, 24B so as to melt and cut the connecting member 22. In consequence, the balloon is separated so as to indwell the blood vessel.

Figure 1:
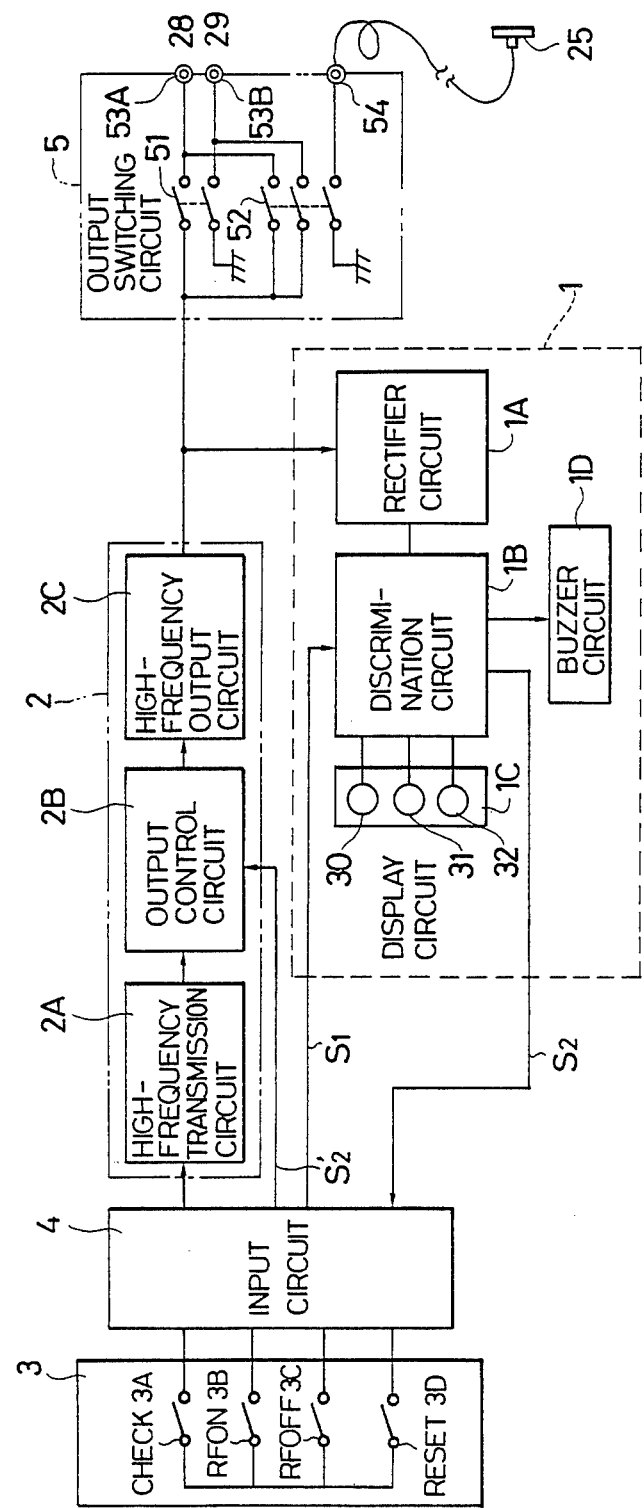
FIG. 1 is a block diagram of an embodiment of a separation device of the present invention for use in a balloon catheter.

A description will be given of an embodiment of the balloon separation device of the present invention suitable for use in a balloon catheter of the type described above. Referring first to FIG. 1 which is a block diagram of the embodiment, the device has a check circuit 1, a high-frequency voltage generating circuit 2, a switch circuit 3, an input circuit 4 and an output switching circuit 5.

Figure 3:
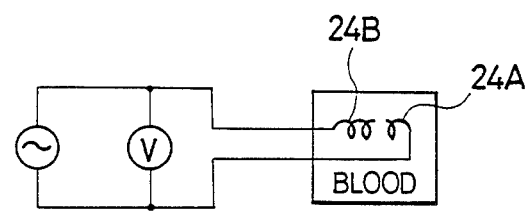
FIG. 3 is a schematic circuit diagram of the device shown in FIG. 1.

The check circuit 1 is intended for checking an electrode circuit including the dipole electrode members 24A, 24B and lead lines 26 and 27 for any abnormality such as cutting or short-circuiting. If there is no abnormality in the electrode circuit, a normal reverse electromotive force is generated in response to a high-frequency voltage applied to the dipole electrode members 24A, 24B. The level of the reverse electromotive force corresponds to the impedance of the blood which is usually between 250 and 1.4 K$\Omega$. When the electrode circuit is in safe or normal condition, the reverse electromotive force or voltage falls within a range corresponding to the above-mentioned range of impedance. However, the voltage falls to zero in the event of a short-circuiting in the electrode circuit, while the voltage rises to the same level as the source voltage in the event of a break or cutting of the lead line. It is therefore possible to check the impedance of the electrode circuit, i.e., to check whether the electrode circuit is in safe condition or not, by measuring the reverse electromotive voltage generated between the dipole electrode members 24A and 24B as shown in FIG. 3 and comparing the measured value with a reference voltage which corresponds to a reference resistance which is obtained when the electrode circuit is in the safe condition.

A detailed description will be given of the embodiment shown in FIG. 1. The switch circuit 3 includes a check switch (CHECK) 3A, a high-frequency power ON switch (RFON) 3B, a high-frequency power off switch (RFOFF) 3C and a reset switch (RESET) 3D. These switches are connected to a high-frequency voltage generation circuit 2 and the check circuit 1 through an input circuit 4.

The high-frequency voltage generation circuit 2 is composed of a high-frequency transmission circuit 2A, an output control circuit 2B and a high-frequency output circuit 2C. The high-frequency transmission circuit 2A is connected to the output control circuit 2B which in turn is connected to the high-frequency output circuit 2C. The input circuit 4 is connected to the output control circuit 2B.

The check circuit 1 includes a rectifier circuit 1A, a discrimination circuit 1B, a display circuit 1C and a buzzer circuit 1D. The rectifier circuit A is connected to the high-frequency output circuit 2C and the discrimination circuit 1B which in turn is connected to the buzzer circuit 1D. The discrimination circuit is connected both to the display circuit 1C and the input circuit 4. The display circuit 1C includes a normal or safe condition indicator lamp 30A for indicating safe condition of the electrode circuit, a line-cut indicator lamp 31A for indicating the cutting of the electrode circuit, and a short-circuit indicator lamp 32A for indicating that a short-circuiting between the electrode members of the dipole electrode or between the lead lines is taking place.

The high-frequency output circuit 2C is connected to the output switching circuit 5.

Figure 4:
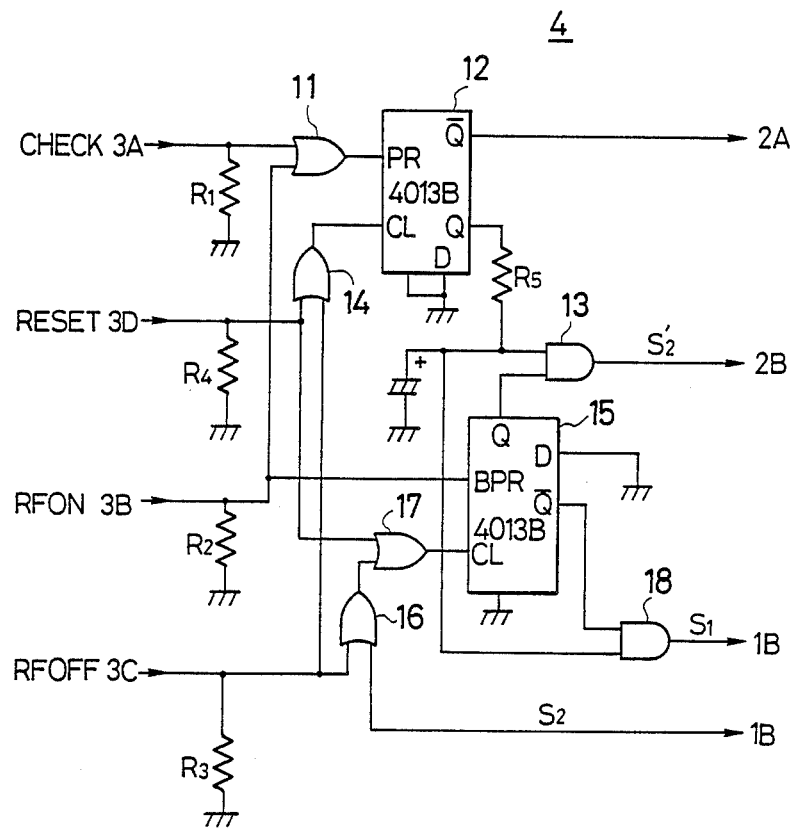
FIG. 4 is a circuit diagram showing the detail of an input circuit in the arrangement shown in FIG. 1.

FIG. 4 illustrates the detail of the input circuit shown in FIG. 1. The check switch CHECK 3A or the high-frequency power ON switch RFON 38 is capable of operating a flip-flop 12 through an OR gate 11. The inversion output Q of the flip-flop 12 is delivered as an ON instruction to the high-frequency transmission circuit 2A. The output Q of the flip-flop 12 is input to the output control circuit 2B through the AND gate 13. In addition, the flip-flop 12 is adapted to be reset by the high-frequency power OFF switch RFOFF 3C or the reset switch RESET 3D through an OR gate 14. The high-frequency power ON switch RFON 3B is adapted for actuating a flip-flop 15 the output Q of which is delivered to the output control circuit 2B through an AND gate 13. The AND gate 13 delivers to the output control circuit 2B a signal $S_2'$ of H level which raises the output level of the high-frequency voltage to an ordinary melt-cut level, on condition that the high-frequency power ON switch RFON 3B has been turned on. Conversely, when the high-frequency power ON switch RFON 3B is off, the AND gate 13 delivers a signal $S'_2$; which lowers the level of the high-frequency voltage to a low level which is to be employed during the checking. The flip-flop 15 is adapted to be reset by the RFOFF 3C through OR gates 16 and 17, as well as by the reset switch RESET 3D through the OR gate 17.

On the other hand, the output Q of the flip-flop 12 and the inversion output Q of the flip-flop 15 are delivered to the discrimination circuit 1B through the AND gate 18. Namely, it delivers the check signal $S_1$ to the discrimination circuit 1B on conditions that the check instruction (CHECK 3A) has been turned on and that the melting instruction (RFON 3B) has not been turned on.

An abnormal signal $S_2$ output from the discrimination circuit 1B resets the flip-flop 15 through OR gates 16 and 17, whereby the output of the high-frequency voltage generation circuit 2 is fixed at low level in the event of any abnormality in the electrode circuit. The arrangement may be such that the output from the high-frequency voltage generation circuit 2 is blocked or cut-off in the event of any abnormality on the electrode circuit.

Figure 5:
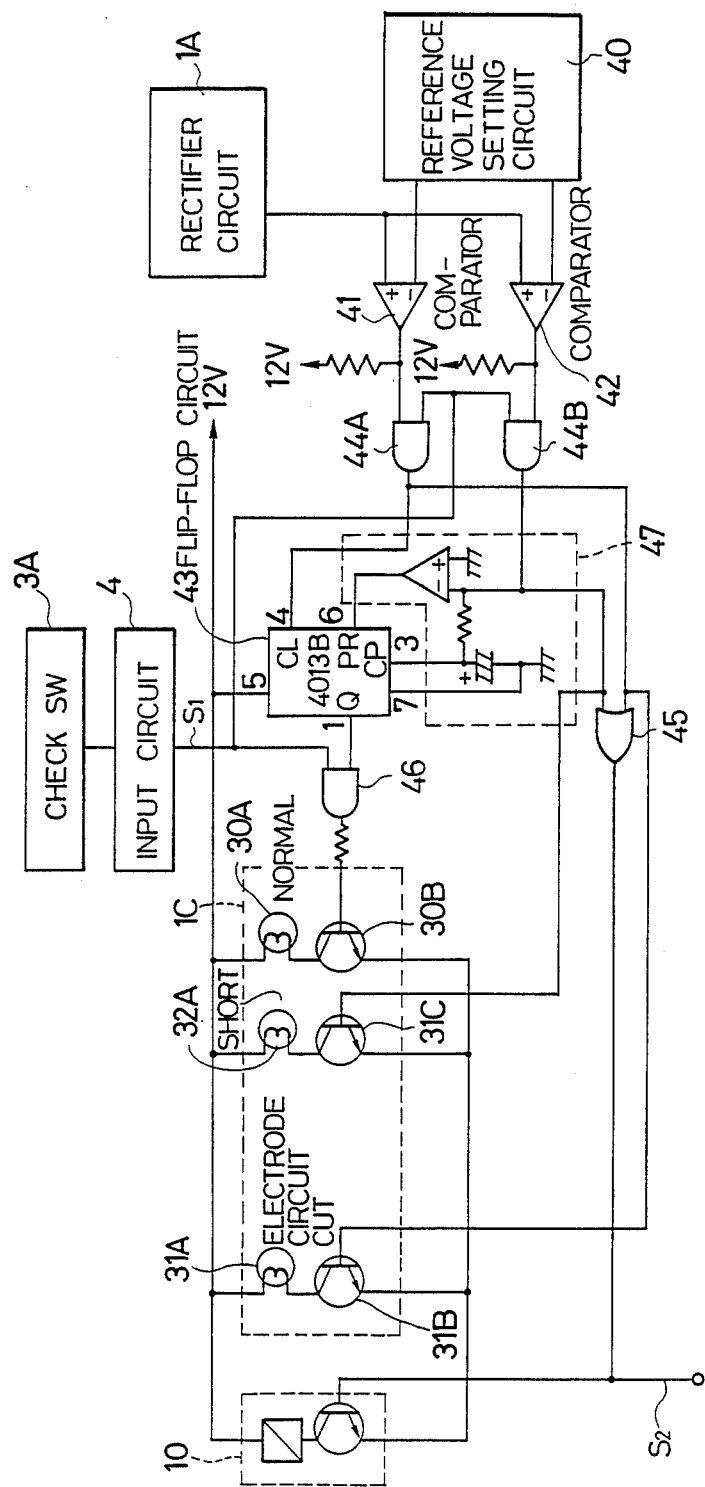
FIG. 5 is an electric circuit diagram of a discrimination circuit and other associated part in the arrangement shown in FIG. 1.

FIG. 5 is an electric circuit diagram of an electric circuit including the discrimination circuit 1B and other associated parts shown in FIG. 1. Referring to this Figure, a reference voltage setting circuit 40 is connected to minus (−) input terminals of a comparator I 41 and a comparator II 42. The rectifier circuit 1A is connected to the plus (+) input terminals of the comparators 41 and 42.

The output end of the comparator 41 is connected to one of the input terminals of an AND gate 44A. The output terminal of the comparator 42 is connected to the one of the input terminals of an AND gate 44B. The output of the AND gate 44A is connected to one of the input terminals of an OR gate 45. The output of the AND gate 44B is connected to the other input terminal of the OR gate 45. The output of the OR gate 45 is connected to the buzzer circuit 1D.

The check instruction $S_1$ output from the input circuit 4 is delivered to one input terminals of the AND gates 44A and 44B. The output of the AND gate 44A is connected to a flip-flop circuit 43. The output of the AND gate 44B is connected to the flip-flop circuit 43 through a delay circuit 47. The flip-flop circuit is connected to one of the input terminals of the AND gate 46 while the other input terminal of the AND gate 46 receives the check instruction $S_1$. The output terminal of the AND gate 46 is connected to a transistor 30B which is capable of selectively turning on the safe condition indicator lamp 30A of the display circuit 1C capable of indicating the safe state of the electrode circuit.

The operation of this embodiment will be described with specific reference to FIG. 6 which is a flow chart showing the flow of the operation.

Figure 6B:
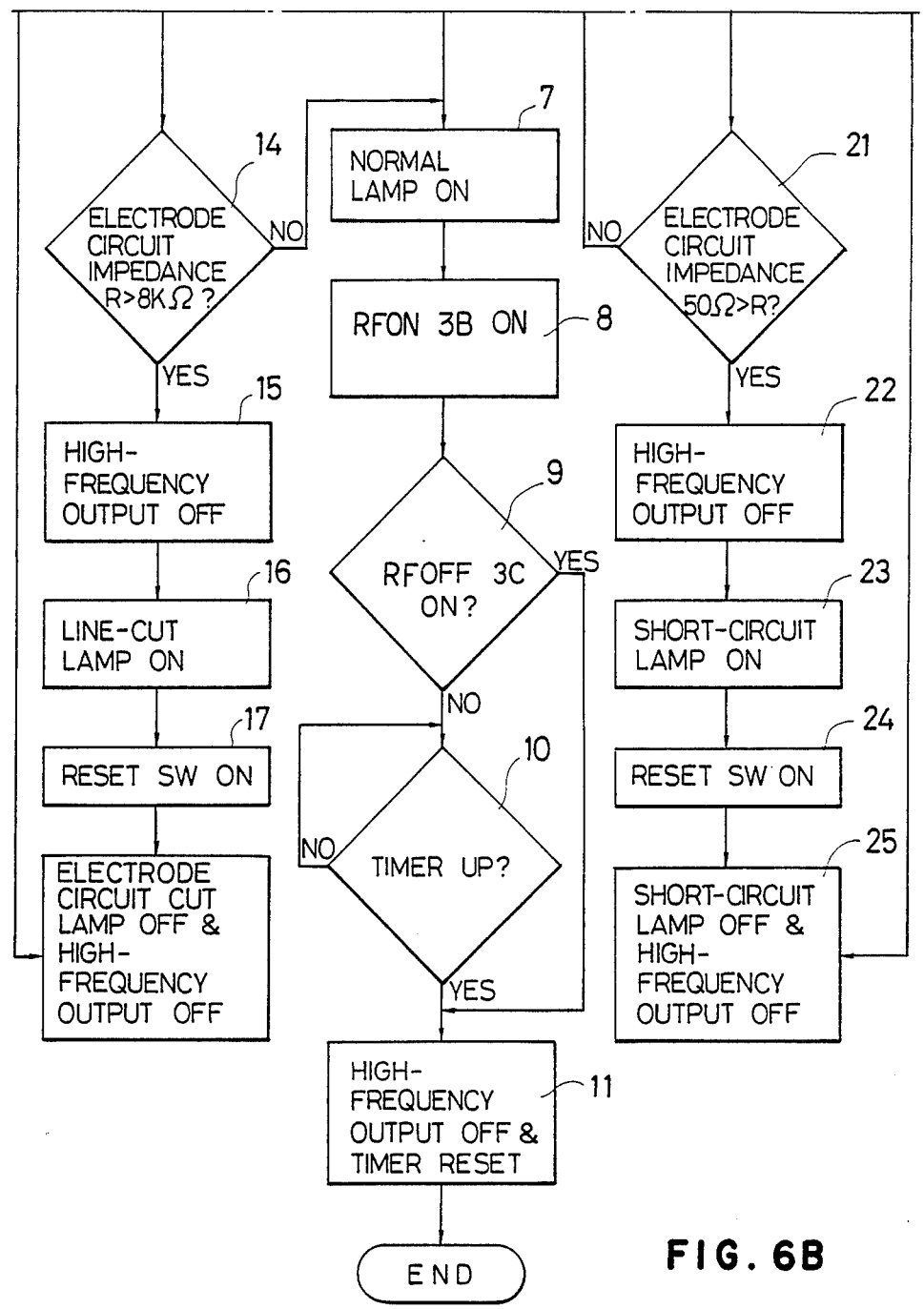
FIG. 6 is a flow chart illustrating the process of operation of the device shown in FIG. 1.

Before execution of the flow of the flow chart shown in FIG. 6, an operation is conducted for setting, by a reference voltage setting circuit 40, a reference voltage which corresponds to the reference impedance which is obtained when the dipole electrode 24A, 24B of the balloon catheter is in the safe condition. Then, local anesthetic operation is effected on the portion of the carotid artery or the femoral artery to be punctured, and the catheter is introduced into the affected part, e.g., affected portion of a cerebral artery, by means of an introducer designed for introducing a catheter. An X-ray contrast media has been charged in the catheter so that the momentary position of the catheter can be observed through an X-ray image. The flow shown in the flow chart of FIG. 6 then begins. In Step 1, the power supply switch of this embodiment is turned on so that the process is started. In Step 2, the lead lines of the electrode members are connected to terminals 53A, 53B of the output switching circuit 5, while a change-over switch 51 is turned on.

In Step 3, the check switch 3A is turned on so that the signal S1 is input to the check circuit 1 through the input circuit 4.

In Step 4, the check circuit 1 is turned on as a result of the turning on of the check switch 3A in the preceding step 3. In consequence, a signal "1" of high (H) level is applied to one input terminals of the comparators 44A, 44B and 46.

When the check switch is turned on in Step 4, a slight voltage of a low level which does not cause the connecting member 22 to be melt down is applied to the electrode members 24A, 24B of the dipole electrode of the balloon, through the high-frequency generating circuit 2A, output control circuit 2B, high-frequency output circuit 2C and the output switching circuit 5. The high-frequency power thus applied is, for example, 300 KHz in frequency and 28 mW in power level.

On the other hand, the on state of the check circuit 1 initiates an operation for determining the impedance between the electrode members 24A, 24B of the catheter. This is conducted by converting the high-frequency reverse electromotive force or voltage generated between the electrode members 24A and 24B into a D.C. current by means of the output switching circuit 5 and the rectifier circuit 1A. Thus, the impedance is determined in the form of a voltage. In general, in the event of a short-circuiting between the electrode members 24A and 24B, the impedance is lowered to 0 to 50, whereas, when cutting in the electrode circuit has taken place, the impedance takes a high value of 8KΩ or higher. The comparators 41 and 42 receive a reference voltage signal from a reference voltage setting circuit 40 so that the reverse electromotive force in the electrode circuit derived from the rectifier circuit 1A is compared with the reference voltage. Namely, by comparing the voltage signal derived from the electrode circuit and the reference voltage with each other, it is possible to discriminate whether the electrode circuit is in the safe condition or any abnormality such as a short-circuiting (impedance 0 to 50Ω) in the electrode circuit or cutting (8KΩ or greater) has taken place in the electrode circuit.

Step 5 executes judgment as to whether the impedance R of the electrode circuit meets the condition of R<50Ω. If the condition is contrary, i.e., if the condition of R>50Ω is met, the process proceeds to Step 6 in which a judgment is executed as to whether the impedance R of the electrode circuit meets the condition of R>8KΩ.

If a condition R<8KΩ is met, the process proceeds to Step 7 in which the electrode circuit is judged to be in safe condition.

Thereafter, a settable liquid such as 2-hydrogen ethylmethacrylate (HEMA) type is charged into the catheter so as to inflate the balloon, and then the operation is executed to separate the balloon.

The operation executed upon judgment of the safe condition of the electrode circuit will be explained with reference to FIG. 5. The arrangement is such that the comparators 41 and 42 produce outputs 0 (zero) when the electrode circuit is judged to be in safe condition. Namely, the outputs from the comparators 41 and 42 are maintained at 0 as long as the impedance between the electrode members 24A and 24B is within the normal range which is generally between 50Ω and 80KΩ. These outputs are delivered to one inputs of the AND gates 44A and 44B while the other inputs of these AND gates 44A, 44B receive signals $S_1$ from the check switch 3A and the input circuit 4. This signal $S_1$ is "1" signal of the high (H) level. The outputs of the AND gates 44A and 44B are not applied to the input of the flip-flop circuit 43 because the outputs from the comparators 41 and 42 are maintained at 0 (zero). The flip-flop circuit 43 therefore maintains its output Q of "1". The output Q of "1" is delivered to one input terminal of the AND gate 46 while the other end of the AND gate 45 receives the check instruction signal $S_1$, so that the AND gate 46 produces an output "1" of the high (H) level, thereby lighting the indicator lamp 30A connected to the output thereof. A delay circuit 47 connected to the flip-flop circuit 43 serves to eliminate any unstable state of the impedance which is caused when the check switch 3A is turned on.

In this state, the process proceeds to Step 8 in which the high-frequency power ON switch RFON 3C is turned on so that the output control circuit 2B is switched by a relay to a state in which it delivers a high-frequency power of, for example, MAX. 30W at 300KHz, large enough to cut the connecting member by a joule heat generated by the resistance of the blood. The output power is adjusted in this state and is increased until the balloon 23 is separated from the catheter body as a result of melting of the connecting member. In this state, the output voltage from the output control circuit 2B is higher than that delivered during the checking of the electrode circuit, so that the comparator I 41 and the comparator II 42 receive a high voltage. The comparator I 41 therefore cannot judge whether this input of the high level is attributable to a cutting of a line in the electrode circuit. Actually, however, the circuit for judging cutting in the electrode circuit does not operate because the inputs of the AND gates 44A, 44B connected to the output of the comparator I 41 receives a signal $S_1$ of the low (L) level when the high-frequency power ON signal RFON 3B is on, so that separation of the balloon is conducted without fail. This applies also to the circuit for judging the occurrence of short-circuiting in the electrode circuit. The connection member 22 is typically made from PVA (polyvinyl alcohol) or TI (trans-polyisoplene). Such a material is softened by heating to about 70° C. so that the connection member 22 can be cut by being heated to this temperature under application of a tension. The process then proceeds to Step 9 in which a judgment is done as to whether the high-frequency power OFF switch REOFF 3C has been turned off. If this switch has been turned on, the process proceeds to Step 11 in which the high-frequency output is turned on. Conversely, if the switch 3C has not been turned on, the process proceeds to Step 10 in which a judgment is executed as to whether a time set in a timer of a timer circuit (not shown) has expired. If the answer is YES, the process proceeds to Step 11 in which the high-frequency output is turned off and, at the same time, the timer of the timer circuit is reset. If time set in the timer has not expired, the high-frequency output is continued to be applied to the electrode members of the catheter for a predetermined period which is, for example, about 5 seconds. The arrangement may be such that a foot switch is used in addition to or in place of the timer so as to enable the operator to freely control the heating time A description will be given of the operation performed when a cut of a line in the electrode circuit has occurred.

When the judgment in Step 6 has proved that the condition of R>8KΩ is met, the process proceeds to Step 12 in which the line cut indicator lamp 31A lights on and the high-frequency power is turned off. This operation will be described with reference to the circuit diagram shown in FIG. 5.

The condition R>8KΩ means that a cut of a line has taken place in the electrode circuit of the balloon catheter. When a line in the electrode circuit has been cut, the impedance between the electrode circuits is increased so that a higher level of the reverse electromotive force or voltage is obtained with the same level of the high-frequency output as that produced in the safe condition. In consequence, the comparator I 41 delivers an output of "1". As a result, the input of the AND gate 44 receives the signal "1" and since the output from the check switch 3A also is "1" the AND gate 44A delivers an output "1" thereby causing the line cut indicator lamp 31A connected to the AND gate 44A to light up. On the other hand, the high (H) level signal of the AND gate 44A is input to the flip-flop circuit 43 and inverted by the same so as to become a low (L) level signal which is delivered to the AND gate 46. Therefore, the safe condition indicator lamp 30A does not light up in the event of a cutting in the electrode circuit. The short-circuiting indicator lamp 32A also is prevented from lighting up because the comparator II 42 delivers an output of the low (L) level.

In the event of a cutting in the electrode circuit, the output "1" from the AND gate 44A is delivered to the OR gate 45 so that the OR gate 45 delivers an output "1" to the buzzer circuit 1D, whereby a buzzer goes off in response to detection of the presence of cutting of a line in the electrode circuit.

On the other hand, the output "1" of the OR gate is input to the input circuit 4 as a high-frequency output OFF signal $S_2$ so that the input circuit 4 produces a signal which maintains the output of the high-frequency voltage transmission circuit at the low level.

The process then proceeds to Step 13 in which the change-over switch 51 is turned off while the change-over switch 52 is turned on in the output switching circuit 5, thus conducting a change-over from a dipole mode to a monopole mode. Then, an electrode plate 25 is adhered to the patient's body and the check switch 3A is turned on again thereby checking whether the impedance between the electrodes 24A, 24B and the electrode plate 25 falls within the predetermined reference range. To this end, the electrode plate 25 is connected to a terminal 54, while the output terminals 53A, 53B of the lead line terminals 28 and 29 are used as a common terminal.

The fact that the condition of $R>8K\Omega$ (R being the impedance of the electrode circuit) is met in Step 14 means that a cutting has taken place in the electrode circuit which is composed of the dipole electrodes 24A, 24B and the lead lines 26 and 27. In this case, the process proceeds to Step 15 in which the high-frequency output is turned off and further to Step 16 in which the line-cut indicator lamp 31A lights up again while the buzzer goes off. In such a case, it is strictly forbidden to charge the settable liquid into the balloon.

Conversely, the fact that the condition of $R<8K\Omega$ is met in Step 14 means that one of the lead lines 26 and 27 is in safe condition. In this case, the settable liquid is charged into the balloon and then the process proceeds to Step 7 in which a high-frequency output is applied between the electrode plate 25 and the electrodes 24A, 24B so as to effect the separation of the balloon 23 by melting of the connecting member 22 by the high-frequency power.

The reset switch 3D is turned on in Step 17 and, in Step 18, the line-cut indicator lamp 31A and the buzzer circuit 1D are turned off. In this case, the catheter has to be replaced with a new catheter because both the lead lines 26 and 27 of the electrode circuit in the catheter inserted into the body have been cut.

A description will be given of the operation which is performed in the event of a short-circuiting occurring in the electrode circuit.

When a condition of $R<50\Omega$ (R being impedance of the electrode circuit) is met in Step 15, it is judged that a short-circuiting is taking place in the electrode circuit. In such a case, the process proceeds to Step 19 in which the short-circuit indicator lamp 32A lights up and the high-frequency output is turned off. This operation will be explained in more detail with specific reference to FIG. 5.

When a short-circuiting has taken place between the electrode members 24A and 24B in the balloon catheter, the impedance between the electrodes is substantially zero so that the reverse electromotive force or voltage induced in the electrode circuit is substantially zero. The comparator II 42 therefore produces an output "1" of high (H) level. This output is delivered to one input terminal of the AND gate 44B the other input of which receives a signal $S_1$ of "1" level, so that the AND gate 44B produces an output "1". As a result, the short-circuit indicator lamp 32A connected to the AND gate 44B lights up. In this case, the normal or safe condition indicator lamp 30A does not light up because the output Q of the flip-flop circuit 43 is 0 (zero). The output from the OR gate 45 is maintained at high (H) level also in the case of a short-circuiting, so that the buzzer is activated as in the case of a cutting in the electrode circuit.

The process then proceeds to Step 20 in which the switches in the output switching circuit 5 is changed-over into monopole mode.

In Step 21, a judgment is executed again as to whether the impedance between the electrodes 24A, 24B in the catheter and the electrode 25 falls within the reference range.

If a condition of $R<50\Omega$ (R being impedance of electrode circuit) is confirmed in Step 22, the process proceeds to a routine including Steps 23 to 25, in which an operation similar to that performed in the event of a cutting in the electrode circuit is executed.

The reason why a high-frequency voltage is used in the described embodiment for the purpose of checking the state of the electrode circuit is as follows. Namely, employment of different frequencies in the checking of the state of the electrode circuit and in the separation of the balloon may cause a difference in the impedance between the normal and abnormal states of the electrode circuit, making it difficult to discriminate the normal and abnormal states from each other. To avoid such an inconvenience, the described embodiment employs the same high-frequency both in the checking of the state of the electrode circuit and the separation of the balloon.

The high-frequency oscillator used in the described embodiment may be, for example, a device which makes use of a base-coupling type tuning coil ordinarily used in AM radios. Such a tuning coil can oscillate a sine-wave signal at a frequency of 300 KHz ± 10%. A peak oscillation output voltage of 2V is obtainable with an input voltage of 12V.

The high-frequency output circuit 2C may be a B-class push-pull amplifier incorporating an output transformer. The output transformer provides a tank circuit capable of being tuned to 300 KHz and produces the maximum output of 13W on condition of $RL=200\Omega$.

What is claimed is:

1. In a balloon catheter having a catheter body and a balloon connected to said catheter body through a connecting member made of a heat-meltable material, said balloon being adapted to be charged with a settable liquid and then be separated from said catheter body as a result of melting of said connecting member by an electric current supplied between at least a pair of electrodes arranged on or in the vicinity of said connecting member, a method of separating said balloon from said catheter body comprising:
measuring the impedance of an electrode circuit which includes said electrodes and lead lines connected to said electrodes;
comparing the measured value of said impedance with a predetermined reference range and judging that, when said measured value does not fall within said reference range, an abnormal condition exists in said electrodes; and
prohibiting the charging of said settable liquid into said balloon when existence of said abnormal condition is detected as a result of the judgment.

2. A method as set forth in claim 1, wherein the measurement of impedance is conducted by measuring a reverse electromotive force generated in said electrode circuit when a predetermined constant voltage is applied to said electrode circuit.

3. A method as set forth in claim 2, wherein the electric current for melting said connecting member is supplied from a high-frequency power supply, and wherein said predetermined constant voltage applied to said electrode circuit for the purpose of measurement of impedance is supplied from said high-frequency power supply.

4. In a balloon catheter having a catheter body, a balloon, a heat-meltable connecting member through which said balloon is connected to said catheter body, and an electrode circuit including at least a pair of electrodes for placement on or in the vicinity of said connecting member, and lead lines connected to said electrodes, an apparatus for separating said balloon from said catheter body comprising:

a melting electric power means for supplying a melting electric current to said electrodes so as to heat-melt said connecting member;

impedance measuring means for measuring the impedance of the electrode circuit; and judging means for comparing the measured value of said impedance with a predetermined reference range and producing an abnormal signal indicative of occurrence of an abnormal state when the measured value of said impedance does not fall within said reference range.

5. An apparatus as set forth in claim 4, wherein said impedance measuring means includes an electric power means for applying a predetermined constant voltage to said electrode circuit, and voltage measuring means for measuring a reverse electromotive force generated in said electrode circuit as a result of application of said predetermined constant voltage, and wherein said judging means compares said reverse electromotive force with said predetermined reference range and produces said abnormal signal when said reverse electromotive force does not fall within said predetermined reference range.

6. An apparatus as set forth in claim 5, wherein said melting electric power means and said constant voltage applying electric power means are capable of producing high-frequency voltages of the same frequency.

7. An apparatus as set forth in claim 6, further comprising alarm means for generating an alarm in response to said abnormal signal.

8. An apparatus as set forth in claim 6, further comprising alarm means for generating an alarm in response to said abnormal signal, and means for preventing, in response to said abnormal signal, the output of said melting electric power means from being applied to said electrodes.

9. An apparatus for separating a balloon from a catheter body of a balloon catheter, comprising:

a switch circuit including first switch means for inputting a check instruction, and second switch means for inputting a balloon separation instruction;

a high-frequency voltage generating circuit for producing a high frequency output, responsively coupled to said switch circuit and being adapted to be started in response to said check instruction or said balloon separation instruction from said first switch means or said second switch means;

output control means operatively coupled to said high-frequency voltage generating circuit for controlling the high frequency output to a predetermined low voltage level, responsive to said check instruction from said first switch means;

an electrode circuit means for effecting balloon separation from the catheter body;

an output circuit means for delivering the high-frequency voltage output from said output control means to the electrode circuit means for balloon separation;

rectifying means responsive to the high frequency voltage output from said output circuit means for producing a rectified output;

judging means for comparing said rectified output with a predetermined reference voltage range and producing an abnormal signal when said output voltage from said rectifying means does not fall within said predetermined reference range, when said judging means receives said check instruction from said first switch means; and alarm means for generating an alarm in response to said abnormal signal.

10. An apparatus as set forth in claim 9, further comprising means for preventing, in response to said abnormal signal, the output of said high-frequency voltage generating circuit from being applied to said electrode circuit means.

11. An apparatus according to claim 9, including a connecting member for connecting the balloon to the catheter body and said electrode circuit means includes at least a pair of electrode members fixed to a surface of said connecting member at a predetermined distance from each other.

12. An apparatus as set forth in claim 10, including a connecting member for connecting the balloon and the catheter body and said electrode circuit means includes at least a pair of electrode members, at least one of said electrode members being fixed to a surface of said connecting member and one of said electrode members comprising an electrode plate adapted to be adhered to the surface of a living body.

13. An apparatus as set forth in claim 9, including a connecting member for connecting the balloon to the catheter body, and wherein said output circuit means includes selectively switchable first and second circuit means, said electrode circuit means comprising first and second pairs of electrodes, said first pair of electrodes being connectable to a surface of said connecting member at a predetermined distance from each other, said second pair of electrodes being connectable to a surface of said connecting member and an electrode plate adapted to be adhered to the surface of a living body.

* * * * *